(12) United States Patent
Baumgartner

(10) Patent No.: US 6,464,071 B2
(45) Date of Patent: Oct. 15, 2002

(54) PACKAGING FOR SURGICAL SUTURE

(75) Inventor: Karl-Heinz Baumgartner, Wedel (DE)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/735,823

(22) Filed: Dec. 13, 2000

(65) Prior Publication Data

US 2001/0000263 A1 Apr. 12, 2001

Related U.S. Application Data

(63) Continuation of application No. 09/315,283, filed on May 20, 1999, now abandoned.

(51) Int. Cl.[7] .............................................. A61B 17/06
(52) U.S. Cl. ..................................................... 206/63.3
(58) Field of Search .............................. 206/63.3, 227, 206/380; 606/228

(56) References Cited

U.S. PATENT DOCUMENTS

| | | | |
|---|---|---|---|
| 4,967,902 A | | 11/1990 | Sobel et al. |
| 5,056,658 A | | 10/1991 | Sobel et al. |
| 5,154,283 A | * | 10/1992 | Brown ....................... 206/63.3 |
| 5,165,217 A | | 11/1992 | Sobel et al. |
| 5,222,978 A | * | 6/1993 | Kaplan et al. ............. 206/83.3 |
| 5,236,083 A | | 8/1993 | Sobel et al. |
| 5,246,104 A | * | 9/1993 | Brown et al. .............. 206/63.3 |
| 5,261,210 A | | 11/1993 | Brown |
| 5,359,831 A | | 11/1994 | Brown et al. |
| 5,417,036 A | | 5/1995 | Brown |
| 5,669,490 A | * | 9/1997 | Colligan et al. ........... 206/63.3 |
| 5,819,918 A | * | 10/1998 | Scanlon ..................... 206/63.3 |
| 6,076,659 A | * | 6/2000 | Baumgartner et al. ..... 206/63.3 |
| 2001/0004966 A1 | * | 6/2001 | Warnecke .................. 206/63.3 |

FOREIGN PATENT DOCUMENTS

FR 15 66 159 A 5/1975

OTHER PUBLICATIONS

Laurence K. Noriega et al., Modern Concepts of Packaging Surgical Needles and Sutures, Medical Progress Through Technology, vol. 20, NR 3/04, pp. 271–179.

* cited by examiner

*Primary Examiner*—Jim Foster
(74) *Attorney, Agent, or Firm*—Emil Richard Skula

(57) ABSTRACT

In a packaging (1) for surgical suture material (6), a thread duct which runs spiral-like is formed in a base (2) and opens at its first end to form a thread removal zone in the periphery area of the base (2). The base (2) is provided with a cover (4). An edge segment (3) of the base (2) can be folded down about a fold line provided in the region of the underside of the base (2) for access to the thread removal zone.

19 Claims, 4 Drawing Sheets

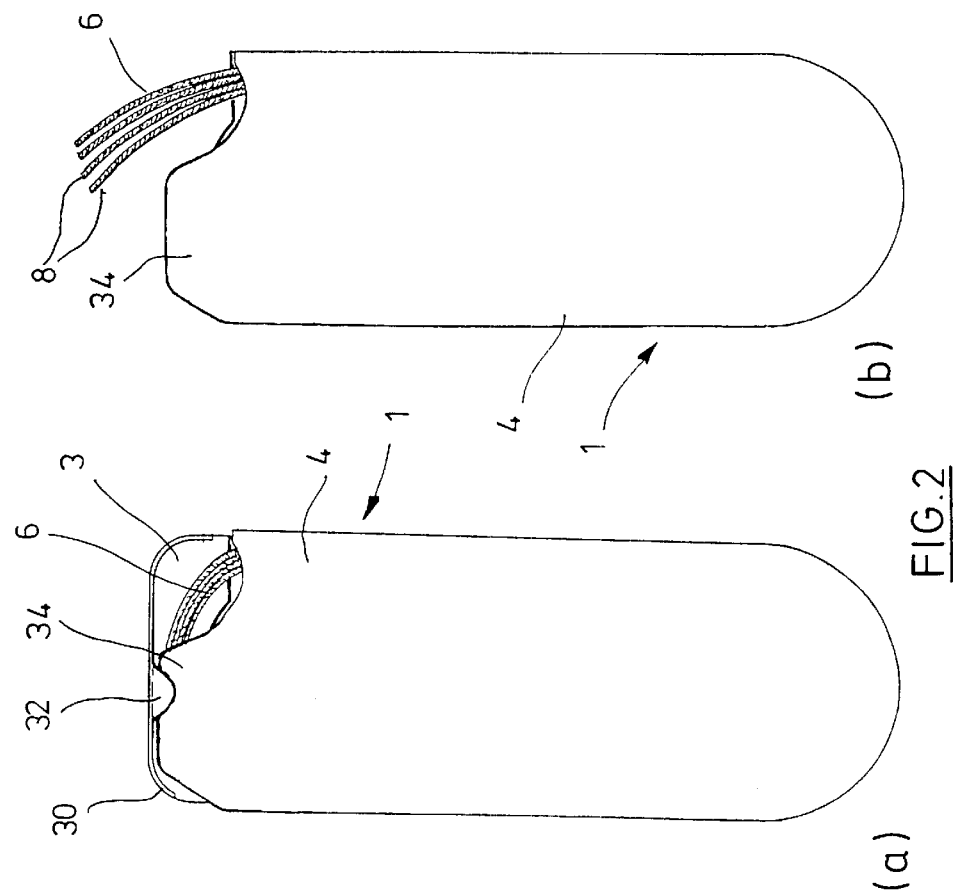
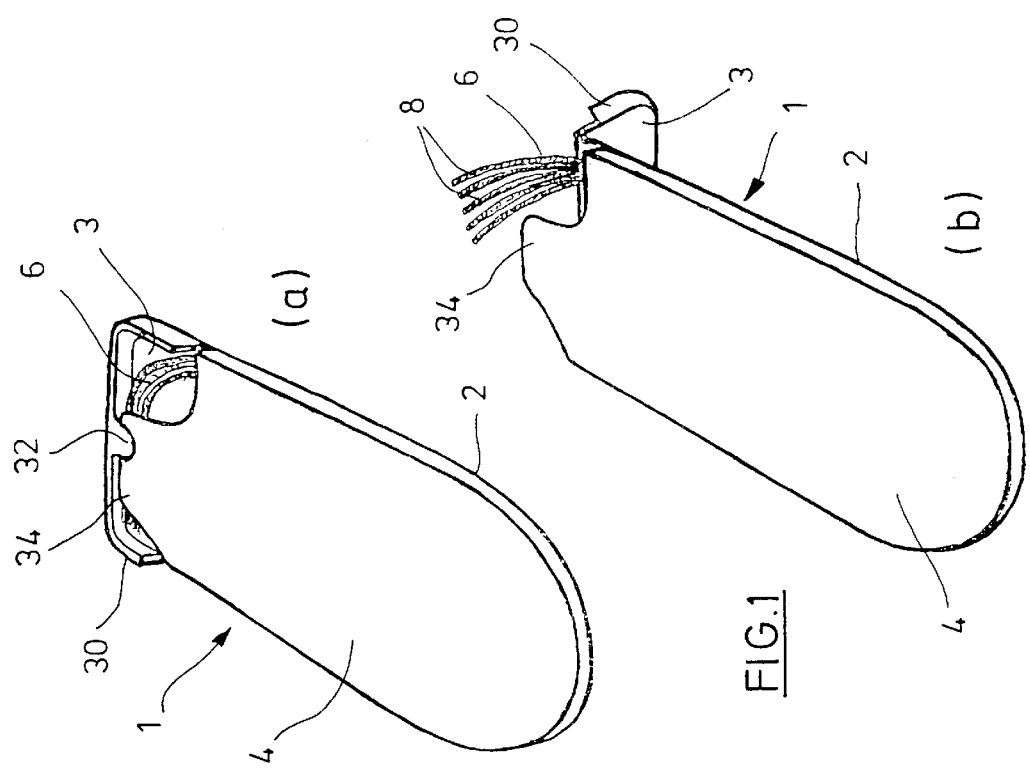

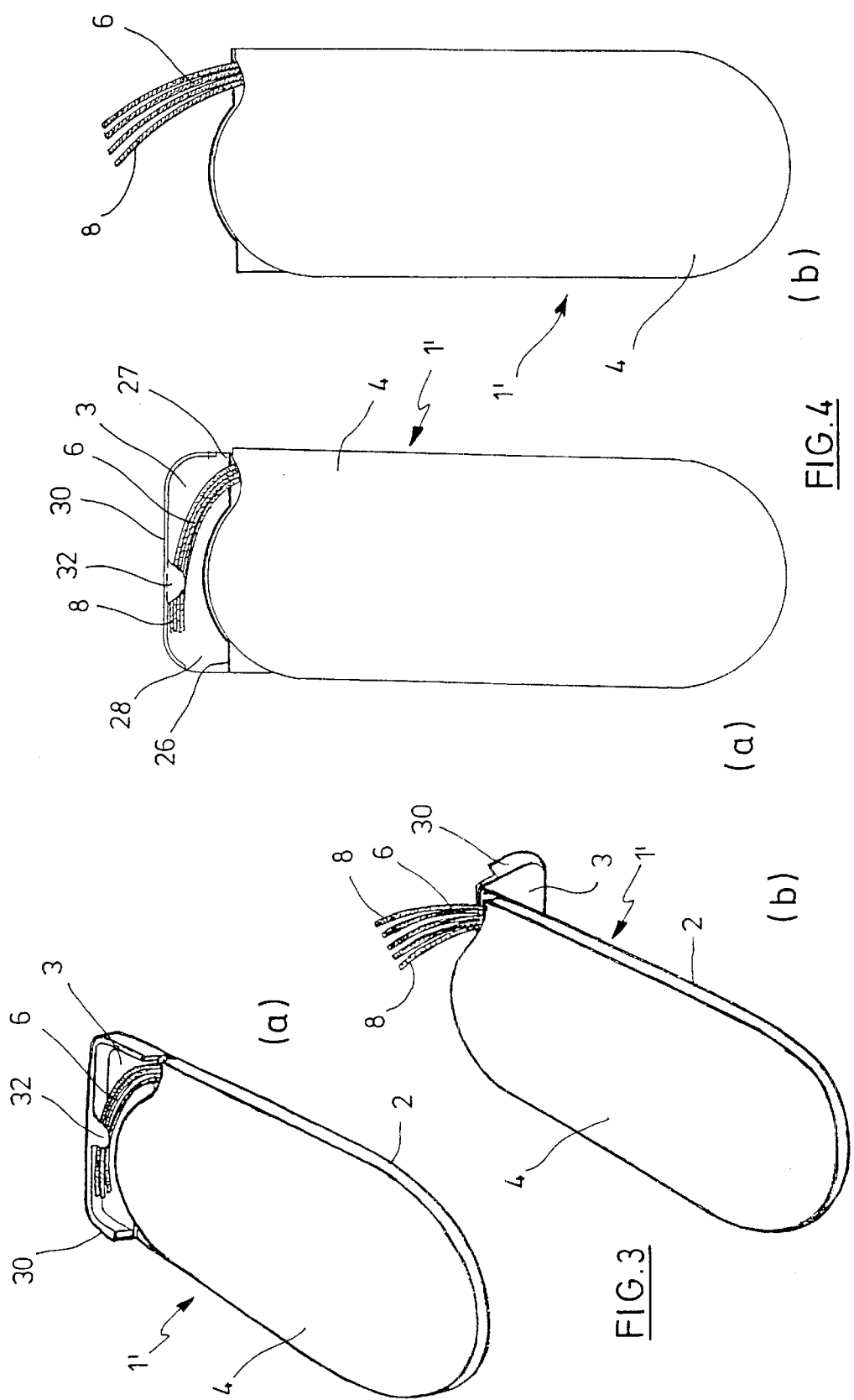

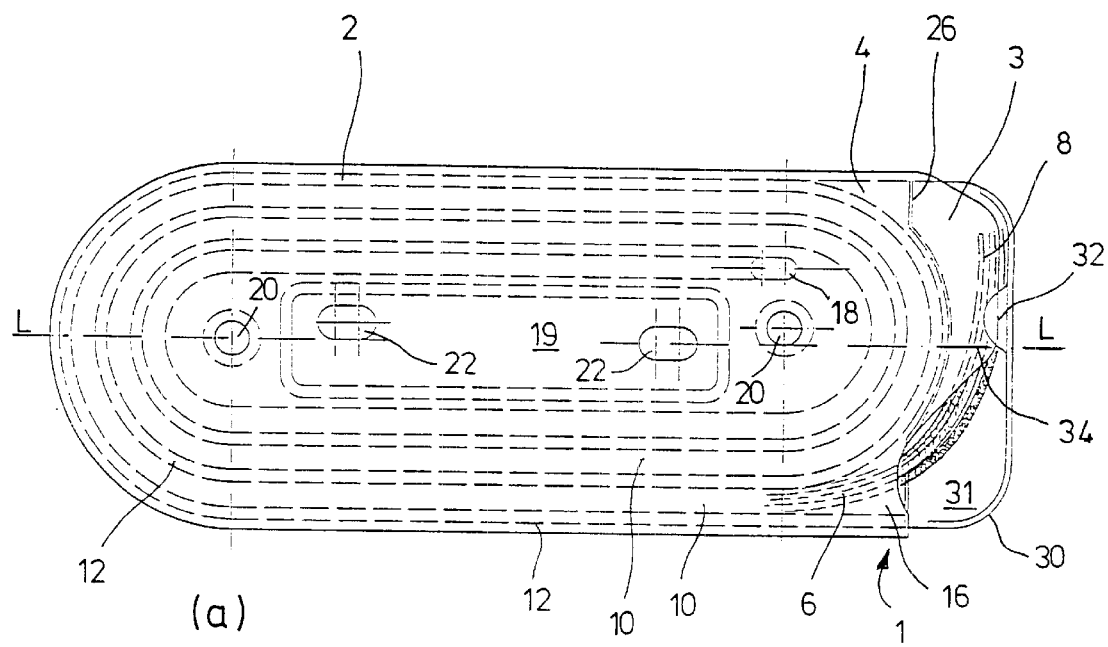
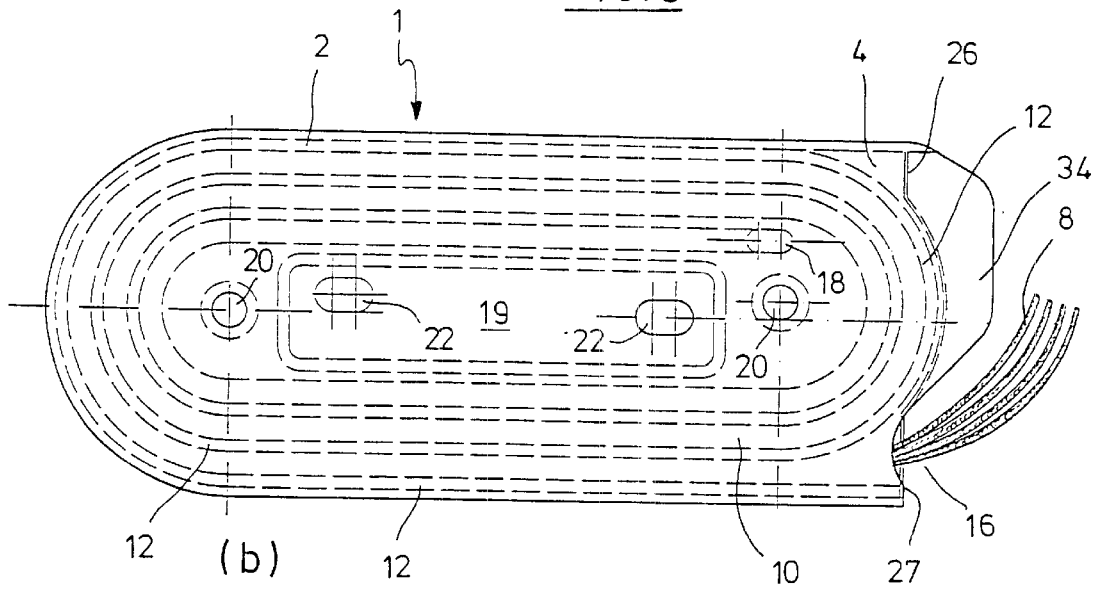
FIG.5

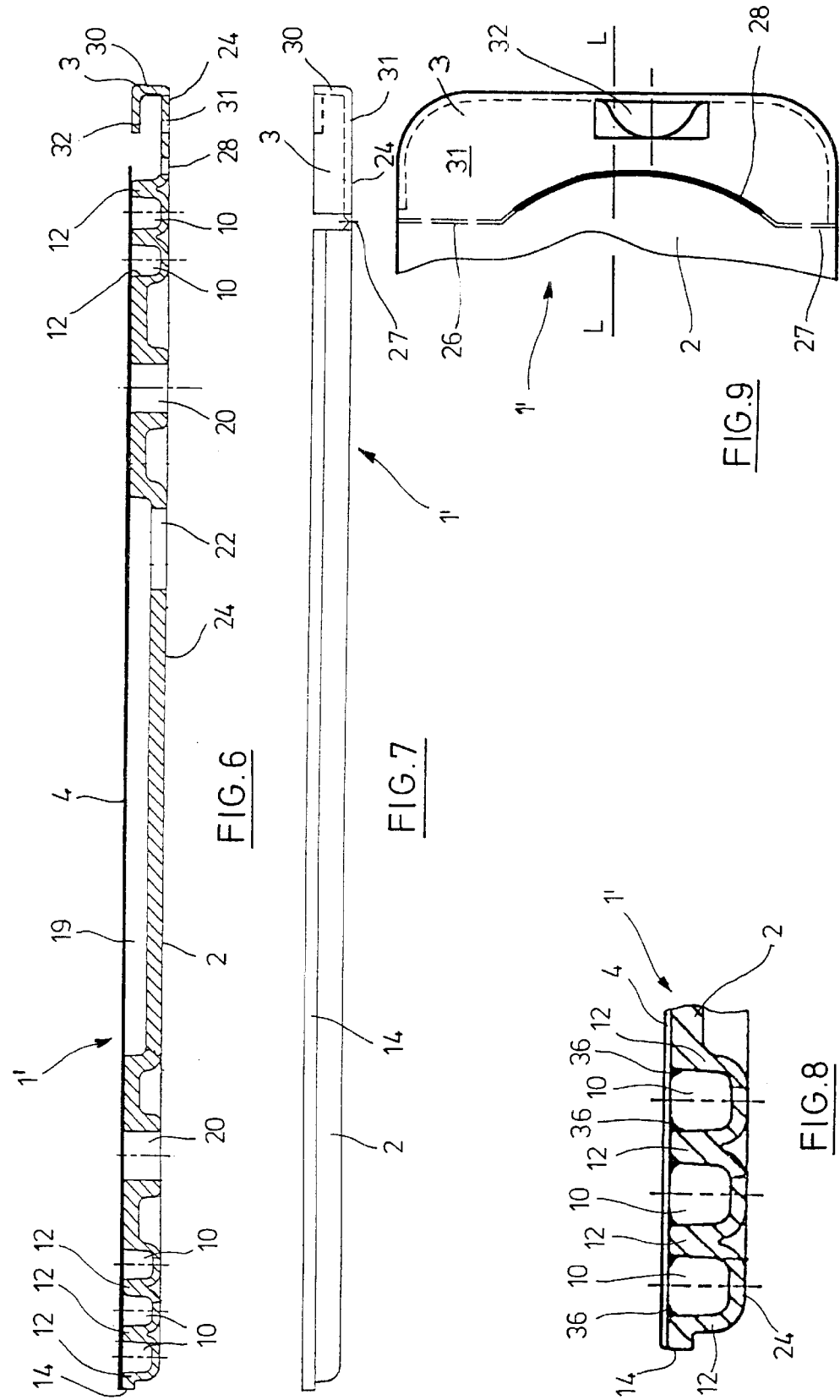

PACKAGING FOR SURGICAL SUTURE

This is a continuation of U.S. application Ser. No. 09/315,283, filed on May 20, 1999, now abandoned.

TECHNICAL FIELD

The invention relates to packaging for surgical suture material, with a base in which a thread duct which runs in a spiral-like way is formed, which opens at its first end to form a thread removal zone in the periphery area of the base, and with a cover for the base.

BACKGROUND OF THE INVENTION

Packages for surgical suture material are known and are described for example in EP 0 471 458 A1. At least one surgical thread can be housed in the thread duct, and can then be removed from the packaging via the thread removal zone after opening the packaging. Being guided through the thread duct is to prevent the surgical thread from sticking or becoming entangled with other thread parts. As the thread duct is constructed in a spiral-like way, relatively long surgical threads can be housed in a compact packaging.

In the packaging for surgical suture material known from EP 0 471 458 A1, there is located at the thread removal zone in the cover an opening through which a needle projects which is attached to the end of a surgical thread stored in the packaging. To remove the suture material, it is necessary to pull on the needle. The thread then slides through the relatively small opening and can rub against the edge of the opening, which is a disadvantage. A further disadvantage of the previously known packaging is that the front end of the thread, here in the area of the point of attachment to the needle, must be guided through the opening in the cover with a fairly small radius of curvature, as the front end area of the thread or the needle is otherwise not safely accessible after the packaging is opened (which is carried out by folding down a flap covering the opening away from the cover). In areas with a small radius of curvature or at kinks, a surgical thread does not generally reassume its original straight form after removal from the packaging (thread memory effect), which is not desired.

DISCLOSURE OF THE INVENTION

The object of the invention is to provide a packaging for surgical suture material from which surgical suture material can be removed easily and without problems, a thread memory effect being essentially avoided.

This object is achieved by a packaging for surgical suture material with the features of claim 1. Advantageous versions of the invention result from the subsidiary claims.

The packaging according to the invention for surgical suture material has a base in which a thread duct running in a spiral-like way is formed. The thread duct opens at one end, its first end, to form a thread removal zone in the periphery area of the base. The packaging also has a cover for the base. An edge segment of the base can be folded down about a fold line provided in the bottom area, preferably on the underside, of the base, for access to the thread removal zone.

In order to open the packaging according to the invention, the edge segment of the base is thus folded down away from the cover so that the thread removal zone is freely accessible. The packaging can then be held so that the cover points upwards and the edge segment can be folded downwards, but also the other way round. Surgical suture material need not be fed through a relatively narrow opening in the cover but instead can be pulled via the freely accessible thread removal zone directly out of the first end of the thread duct. Surgical suture thread situated in the packaging can therefore be laid so that no unwanted kinks form. The thread duct can serve to house one, but also several surgical threads. The packaging according to the invention is particularly suited to needleless suture material, i.e. for surgical threads to which no surgical needle is attached, but can also be used for threads with needles. In this case, the thread removal zone serves to house the surgical needle or needles when the packaging is unopened. To avoid a thread memory effect, it is advantageous to have the thread removal zone situated in the periphery area of the base, as the initially more closely wound coils of a surgical thread which are located in the inner area of the packaging when packed are extended to ever-greater radii of curvature when pulled out through the thread duct.

In a preferred version of the packaging according to the invention, the edge segment has a raised wall of the height of the thread duct, which extends along the periphery of the base. The wall need not run over the entire periphery of the edge segment as, if the packaging is stored in a tight outer wrapper, it also remains sterile if it has openings itself. A stop lug preferably extends from the raised wall.

In a preferred version, the stop lug is constructed to hold one edge of the cover when the edge segment is not folded down. On the one hand, therefore, the down-foldable edge segment can be locked at the cover with the help of the stop lug. On the other hand, the raised wall ensures, depending on the design in co-operation with the stop lug, that the surgical threads contained in the packaging lie curved in the area of the thread removal zone prior to opening and do not come into contact with an outer wrapper, e.g. a foil outer wrapper. When the edge segment is folded down, the stop lug disengages from the cover and the end areas of the surgical threads located in the thread removal zone are no longer held by the raised wall or the stop lug. They tend therefore to straighten up so that the end areas of the threads or the surgical needles attached to them project from the packaging. It is therefore easy to grip an individual thread end (or where appropriate the surgical needle attached to it) and to pull the corresponding surgical thread out of the thread duct. If several threads are contained in the packaging, these can be removed bundled if necessary.

In a similar preferred version, the stop lug is designed to hold the end area of one or more surgical threads contained in the packaging when the edge segment is not folded down (packaging in the closed state). The stop lug can additionally engage at the edge of the cover, but it need not. In the latter case, the stop lug, acting in cooperation with the section of the raised wall from which it extends, holds the thread end areas laid curved (or where appropriate the surgical needles attached to them) when the packaging is closed. The surgical suture material is removed in a similar way to the previous version. When the edge segment is folded down, the curved thread areas spring from the stop lug and more or less straighten up. Thus any thread end can easily be individually gripped and the corresponding surgical thread can be pulled out of the packaging. If necessary, a bundle of surgical threads can also be removed as a whole.

The cover is preferably constructed as a flat sheet and can contain cardboard or paper, the cover preferably containing polyethylene or polypropylene on its underside facing the base. The cover can for example consist of a sheet or film made from polyethylene or polypropylene. In a particularly advantageous version of the invention, the cover is made from a piece of cardboard which is coated on its underside with polyethylene. A cover of this kind has various advantages. Cardboard is suitable for imprinting, so that the packaging can be easily provided with a product label. Furthermore, cardboard acts as a hydrostore, i.e. it is able to absorb residual quantities of water after a packaging with surgical suture material has been introduced into a tight outer wrapper. The cover seals off the thread duct to the top and thus protects the surgical suture material contained in it. Such a cover acts as a lid for the base and thus reinforces the entire package. Furthermore, the paper fibres of the cardboard are bound by the polyethylene coating on the side of cover facing the surgical suture material so that no contamination of the product contained in the packaging can occur. In principle the cover can be glued onto the base for example by dispersion varnish or adhesive, but is sealed up in the particularly advantageous version (see below).

The base is preferably formed as an injection-moulded part and can consist of polyethylene or polypropylene. Injection-moulded parts can be prepared in large quantities at favourable cost and with high precision.

In the particularly advantageous version mentioned, the cover is sealed onto the base which is made from polyethylene in this case. To do this, the cover or the base or both components are heated so that the two facing surfaces containing polyethylene melt together. The temperature and contact pressure are preferably chosen so that a bead forms to the cover in the upper end area of the thread duct wall. This bead forms from surplus melted polyethylene which is pulled from the duct wall in a furrow-like manner to the polyethylene coating on the underside of the cover, as a result of intermolecular interactions. The bead formation has the advantage that gaps are reliably avoided between the upper end area of the duct wall and the cover. Therefore there is no need to fear that, when surgical suture material is removed, a thread becomes stuck or pulled tight in such a gap, which would be a great disadvantage. The particularly advantageous version of the packaging according to the invention for surgical suture material cannot just be cheaply produced, but also has a cross-section form of the thread duct which enables the thread to be withdrawn safely.

The fold line is preferably constructed as a film hinge. The fold line can have at least two sections lying on a straight line which are connected via an opening or a broken line in the base. Such a break in the fold line can be necessary for design reasons if for example a part of the thread duct wall projects above the break, which would prevent the edge segment from being folded down.

In a preferred version of the invention, the base and/or the cover has an opening in the area of the second end of the thread duct. To fill the packaging with surgical suture material, a below-atmospheric pressure can be applied at this opening. In this way, surgical threads which are inserted into the first end of the thread duct with their ends opposite to the end considered up to now can be sucked into the first end of the thread duct without problems.

The packaging according to the invention for surgical suture material can thus be produced cheaply and is simple and reliable in handling. In particular, the packaging can be easily and quickly opened, and, when the surgical suture material is removed, the threads are minimally damaged at most, as they are neither caught nor squashed nor bent. If only the base and the cover are used as components and the foldable edge segment is connected in one piece with the rest of the base, there are no loose parts or parts to be loosened. Furthermore, the packaging can have a small overall height, which reduces the storage and transport costs. In principle, similarly constructed packagings can be used for completely different thread lengths and also thread numbers.

The invention is described in more detail in the following by means of embodiments.

BRIEF DESCRIPTION OF THE DRAWINGS

FIG. 1 a perspective view of a first version of a packaging according to the invention for surgical suture material, in part (a) in the closed state and in part (b) in the opened state.

FIG. 2 a plan view of the version according to FIG. 1, in part (a) in the closed state and in part (b) in the opened state.

FIG. 3 a perspective view of a second version of a packaging according to the invention for surgical suture material, in part (a) in the closed state and in part (b) in the opened state.

FIG. 4 a plan view of the version according to FIG. 3, in part (a) in the closed state and in part (b) in the opened state.

FIG. 5 a plan view of the version according to FIG. 1, areas which are not directly visible being represented in broken lines, in part (a) in the closed state and in part (b) in the opened state.

FIG. 6 a longitudinal section through the version according to FIG. 3 along the longitudinal axis.

FIG. 7 a side view of the version according to FIG. 3, areas which are not directly visible being represented in broken lines.

FIG. 8 an enlarged view of the left-hand area of FIG. 6.

FIG. 9 a diagrammatic view of the edge segment of the version according to FIG. 3 from underneath.

DETAILED DESCRIPTION OF THE PREFERRED EMBODIMENTS

A first version of a packaging 1 for surgical suture material is shown in FIG. 1 in perspective view. The packaging 1 has a base 2 with an edge segment 3. A thread duct which runs in a spiral-like way is formed in the base 2 (see FIG. 5). A cover 4 is situated above the base 2. Housed in the packaging 1 are a plurality of surgical threads 6 which are needleless in the example, but which can also be provided with surgical needles. In part (a), FIG. 1 shows the closed state of packaging 1, i.e. a state in which the edge segment 3 is not folded away from the rest of the base 2. As explained below in detail, the edge segment 3 can be folded downwards or swivelled away about a fold line provided on the underside of the base 2, so that the state shown in part (b) of FIG. 1 is achieved. In this state, the end areas 8 of the surgical threads 6 are no longer constricted by the edge segment 3 so that they fan out slightly, as shown in FIG. 1 part (b). It is then readily possible to grip an individual surgical thread 6 by its end area 8 and pull it out of the packaging 1. FIG. 2 corresponds to FIG. 1, but shows a plan view of the packaging 1.

FIGS. 3 and 4 are analogous representations of a second version of a packaging 1' for surgical suture material. The packaging 1' differs from packaging 1 simply in the formation of the cover 4 in the area of the edge segment 3 of the base 2. Thus the same reference numbers are used for both versions.

The base 2 with the edge segment 3 is formed in the embodiments in one piece as an injection-moulded part and is composed of polyethylene. Other materials such as for example polypropylene are also conceivable.

The cover 4 is made from cardboard in the embodiment and is coated with polyethylene on its underside, i.e. the side facing the base 2. A strong bond between cardboard and polyethylene can be produced for example by rolling a polyethylene film hot onto cardboard, the polyethylene softening and penetrating into the pores present in the cardboard, or by spraying polyethylene.

The structure of the base 2, which is the same in the two respective versions of the packaging 1 and 1', is explained further in the following using FIGS. 5 to 9.

As FIGS. 5 and 6 in particular show, a thread duct 10, running in a spiral-like way and defined by a thread duct wall 12 is formed in the base 2. The thread duct wall 12 limits the packaging 1 or 1' towards the outside, i.e. at its periphery, and in addition separates the individual coils of the thread duct 10 from one other. At the outer periphery of the packaging 1 or 1', the thread duct wall 12 carries a strengthening edge 14 (see FIG. 6 and FIG. 7). The thread duct 10 opens at one end, its first end, to form thread removal zone 16, which is located in the periphery area of the base 2, see FIG. 5. At its other end, the second end, there is an opening 18 on the underside of the base 2, see FIG. 5. If a below atmospheric pressure is applied at the opening 18, surgical threads 6 can be sucked into the packaging 1 or 1 (see below).

The middle region of the base 2 is occupied by a cavity 19 which is not connected to the thread duct 10. Auxiliary openings 20 and 22 facilitate the handling of the packaging 1 or 1' during manufacture and filling with surgical suture material.

The region of the base 2 shown on the right-hand side in FIGS. 5, 6 and 7 is formed by the edge segment 3. The edge segment 3 can be folded downwards about a fold line provided on the underside 24 of the base 2 for access to the thread removal zone 16, as already seen. The fold line has two sections 26 and 27, see in particular FIG. 7 and the schematic representation according to FIG. 9, and is constructed as a film hinge (see FIG. 7). The facing ends of the sections 26 and 27 are connected to each other by a broken line 28, i.e. by an opening which is formed in the base 2 (see FIG. 6). The broken line 28 is provided because a curved region of the thread duct wall 12 extends from the adjacent bottom zone, see in particular FIG. 5 part (b), which is not to be foldable with the edge segment 3.

The major part of the outer periphery of the edge segment 3 is occupied by a raised wall 30, see in particular FIG. 5 part (a) and FIG. 6, which starts from the bottom, numbered 31, of the edge segment 3, and is about as high as the thread duct wall 12. From the upper end of the raised wall 30, a stop lug (securing lug) 32 projects inwards in the vicinity of the longitudinal axis L-L of the packaging 1 or 1', see in particular FIG. 5 part (a), FIG. 6 and FIG. 9. One edge 34 of the cover 4 is clamped under the stop lug 32 in packaging 1 when packaging 1 is in the closed state, thus in the state in which the edge segment 3 is not folded down, see FIG. 1 part (a), FIG. 2 part (a) and FIG. 5 part (a). In the other version, packaging 1', on the other hand, in this state the stop lug 32 holds the end areas 8 of the surgical threads 6 directly, as shown in FIG. 3 part (a) and FIG. 4 part (a). In this version, the cover 4 does not extend beneath the stop lug 32, see FIG. 6.

In the embodiments, the cover 4 is sealed on the base 2. As the cover 4 is coated with polyethylene on its underside, this polyethylene fuses, when heated, with the polyethylene on the upper side of the thread duct walls 12 of the base 2. In the upper end area of the thread duct wall 12 to the cover 4 beads 36 form as drawn in black in FIG. 8. These beads prevent a thread 6, which is located inside the thread duct 10, from being pulled into any intermediate space between the base 2 and the cover 4 and sticking there, when it is being pulled out. Thus in the versions described, the cover 4 can be easily secured on the base 2 by being sealed on, which results in a thread duct 10 being closed in cross-section, from which thread removal is possible without problems.

To fill the packaging 1 or 1' with surgical suture material, the surgical threads 6 to be introduced are inserted as a bundle into the thread removal zone 16 with their ends opposite the end areas 8, after the cover 4 is secured onto the base 2. The edge segment 3 can be in the non-folded state, as the thread removal zone 16 is also accessible from above because of the cut-out of the cover 4. A below-atmospheric pressure is then applied to the opening 18, as a result of which the surgical threads 6 are sucked into the thread duct 10. After this process is over, only their end areas 8 still project from the thread duct 10. The end areas 8 of the surgical threads 6 are then clamped under the stop lug 32, either directly (packaging 1') or under the edge 34 of the cover 4 which is held by the stop lug 32 (packaging 1).

The packaging 1 or 1' is preferably stored in a gastight sealed outer wrapper which consists for example of aluminium foil or aluminized plastics film. As the glued or sealed seams of such an outer wrapper are not normally absolutely tight, the cardboard material used in the embodiments for the cover 4 has the advantage that it absorbs moisture that penetrates these seams in the course of time, and in this way keeps it away from the suture material. Surgical threads 6, which are manufactured for example from hydrolytically degradable resorbable material, would lose their strength under the influence of moisture. The cardboard material of the cover 4 has the further advantage that identifying descriptions for the suture material located in the packaging 1 or 1' can be printed on the upper side of the cover 4.

To use the packaging 1 or 1', it is first removed from the outer wrapper mentioned. Then, the edge segment 3 can be folded down without difficulty, whereby the end areas 8 of the surgical threads 6, as already explained, become freely accessible. The end areas 8 can thus be gripped without problems in order to pull out individual surgical threads 6 from the packaging 1 or 1'. The thread duct 10 which runs spiral-like guides the surgical threads 6 securely so that they do not become entangled or knotted with each other and, when the desired thread is pulled out, the surgical threads 6 remaining in the thread duct 10 are displaced only to a negligible degree.

What is claimed is:

1. A suture package, comprising a base having a thread duct which runs in a spiral-like fashion and which opens at a first end thereof to form a thread removal zone in a periphery area of said base, said base including a fold line and an edge segment which is foldable at said fold line so as to permit access to said thread removal zone; and a cover connected to said base.

2. The suture package of claim 1, wherein said fold line of said base includes a plurality of film hinges; and wherein said base has an arcuate slit-like opening located between said film hinges.

3. The suture package of claim 1, wherein said base includes an opening at a second end of said thread duct.

4. The suture package of claim 1, wherein said cover includes an opening at a second end of said thread duct.

5. The suture package of claim 1, wherein said edge segment is foldable between a closed position, in which said edge segment constricts free ends of threads projecting from said thread duct, and an open position, in which said edge segment does not constrict the free thread ends.

6. The suture package of claim 5, wherein said edge segment of said base has a raised side wall and a stop lug extending from said raised side wall, said stop lug being sized and shaped to be in contact with an adjacent edge of said cover when said edge segment is in its said closed position.

7. The suture package of claim 5, wherein said edge segment of said base has a raised side wall and a stop lug extending from said raised side wall, said stop lug being spaced from an adjacent edge of said cover when said edge segment is in its said closed position.

8. The suture package of claim 1, wherein said cover is a flat sheet and is sized and shaped to overlie said thread duct.

9. The suture package of claim 8, wherein said cover contains cardboard.

10. The suture package of claim 8, wherein said cover contains paper.

11. The suture package of claim 8, wherein said cover has an inner surface which faces said base and which contains polyethylene.

12. The suture package of claim 8, wherein said cover has an inner surface which faces said base and which contains polypropylene.

13. The suture package of claim 1, wherein said base is formed as an injection-molded part.

14. The suture package of claim 13, wherein said base is made of polyethylene.

15. The suture package of claim 13, wherein said base is made of polypropylene.

16. The suture package of claim 1, wherein said cover is sealed on said base.

17. The suture package of claim 16, wherein said thread duct is defined by a thread duct wall having a plurality of beads formed in an upper end area of said thread duct wall adjacent to said cover.

18. The suture package of claim 1, wherein said base has an outer surface and wherein said fold line is located on said outer surface.

19. The suture package of claim 1, wherein said edge segment of said base includes a raised side wall having a height and said thread duct has a depth which is substantially the same as said height of said raised side wall.

* * * * *